United States Patent [19]

Casselman, deceased, Arthur R. et al.

[11] Patent Number: Plant 5,650

[45] Date of Patent: Jan. 28, 1986

[54] PLUM TREE "RAY'S HOPE"

[76] Inventors: Casselman, deceased, Arthur R., late of Exeter, Calif.; Jessie M. Casselman, legal representative, 257 S. Quince, Exeter, Calif. 93221

[21] Appl. No.: 576,487

[22] Filed: Feb. 2, 1984

[51] Int. Cl.[4] ..... A01H 5/03

[52] U.S. Cl. ..... Plt./38

[58] Field of Search ..... Plt./38

*Primary Examiner*—Robert E. Bagwill

*Attorney, Agent, or Firm*—Worrel & Worrel

[57] ABSTRACT

A plum tree broadly characterized by its general resemblance to the Casselman Plum Tree in its regular and productive bearing of medium-sized fruit having firm flesh but which ripens four to five weeks after that of the Casselman Plum Tree.

1 Drawing Figure

BACKGROUND OF THE NEW VARIETY

The present invention relates to a new and distinct variety of plum tree which has been denominated varietally as "Ray's Hope" and which is broadly similar to the unpatented Casselman Plum Tree of which it is a sport but from which it differs in bearing fruit which ripens at least one month later than that of the Casselman variety.

The Casselman variety of plum tree is well known commercially as a vigorous and productive bearer of attractive, medium-sized, red colored fruit having a size and shape similar to that of the Late Santa Rosa variety. Because the Casselman Plum Tree enjoys a reputation of producing fruit having firm, juicy flesh of sweet, mild flavor, it has been recognized as desirable to provide a plum tree bearing fuit of similar size and shape and flavor characteristics but which ripens later in the season than does the Casselman plum, thereby effectively extending the period during which similar commercially attractive plums can continuously be marketed.

ORIGIN AND ASEXUAL REPRODUCTION OF THE NEW VARIETY

The new variety of plum tree was discovered by my husband, Arthur R. Casselman, now deceased, in 1974 growing as a sport on a Casselman plum tree in an orchard of Casselman plum trees leased by the discoverer from Violia Casselman, the mother of the discoverer, also now deceased, and located at 18596 Avenue 296 in the City of Exeter, in the State of California.

The new variety was asexually reproduced in May of 1979 at the direction of Arthur R. Casselman by budding on Marianna plum stock in a nursery owned by Bob Reisner located on South Farmersville Avenue in Farmersville, Calif. The reproduced trees were subsequently transplanted to an orchard owned by Arthur and Jessie M. Casselman, located at 275 South Quince Avenue, Exeter, Calif., where they are now located. The fruit and tree characteristics resulting from this budding have proved identical to those of the original mutation in all respects.

SUMMARY OF THE NEW VARIETY

The instant variety of plum tree is characterized by perpetuating the general characteristics of the Casselman Plum Tree (unpatented) in its heavy production of uniformly medium-sized, clingstone fruit which ripens four to five weeks later than that of the Casselman plum tree.

The fruit has firm meat with excellent taste and exhibits excellent storage qualities.

The new plum tree bears fruit whose skin attains a color of dark red (Plate 7-L-5) to light red-orange (Plate 5-K-11) on a ground color of yellow (Plate 10-J-5), maturing between the first and third weeks of September and having a light yellow-amber (Plate 9-J-6) colored flesh with few, fine and tender fibers.

BRIEF DESCRIPTION OF THE DRAWING

The accompanying drawing is a color photograph of five mature plums of the subject variety with one of the fruits divided along the suture plane to show the flesh color and stone characteristics, together with representative twigs bearing characteristic leaves and a detached leaf disposed to show the lower surface thereof.

DETAILED DESCRIPTION

Referring more specifically to the pomological details of the new and distinct variety of plum tree, the following has been observed under the ecological conditions prevailing in the designated orchard in Tulare County, Calif. All color code plate identifications are by reference to the Maerz and Paul *Dictionary of Color,* Second Edition, 1950.

TREE

Figure: Upright, spreading.
Productivity: Productive.
Regularity of bearing: Regular.
Vigor: Vigorous.
Trunk:
- *Diameter in relation to length.*—Medium.
- *Surface characteristics.*—Medium surface texture.
- *Color.*—Variable, mostly gray brown (Plate 15-C-6).
- *Lenticels.*—Numerous.

Branches:
- *Size.*—Medium.
- *Surface texture.*—Smooth.
- *Color.*—Mature, one-year old shoots, light brown (Plate 14-D-12); new shoots, green (Plate 19-H-5).

Leaves:
- *Size.*—Medium to large.

*Length.*—14.0 cm.
*Width.*—6.1 cm. (measurements from leaves growing at midpoint of vigorous upright shoots).
*Color.*—Upper surface — Dark green (Plate 24-L-4); Lower surface — Light green-gray (Plate 22-D-5).
*Leaf margin.*—Coarsely crenate, single from base of leaf blade to below mid-margin; often double from mid-margin to apex. Crenations usually tipped with a small brown gland. Leaf blade slightly undulate along margins.
*Petiole.*—Medium size; average length — 15 to 18 mm.; thickness — 1.5 mm.
*Color.*—Light green (Plate 17-D-3).
*Stem gland.*—Number — One or two; arrangement — alternate in position on very base of leaf blade.
*Size.*—Small.
*Form.*—Mixed, most often reniform.
*Color.*—Light green when young (Plate 17-H-5), darkening and deteriorating with age.
*Stipules.*—Number — Two at base of petiole, usually persistent.
*Size.*—Small, narrow.
*Length.*—8 to 11 mm. at maturity.
*Width.*—Average 1 mm.
*Color.*—Light green (Plate 17-J-5) when young, darkening with maturity.

Flower buds:
*Size.*—Small.
*Shape.*—Narrow, conic.
*Color.*—Brown scales (Plate 14-D-10). Free from stem.

FRUIT

Maturity:
*First pick in* 1983.—September 10.
*Last pick.*—October 3.
*Firm at full commercial maturity.*—September 23 in 1983.

Size.
*Uniformity.*—Uniformly medium.
*Diameter.*—Cheek — 48 mm.; transverse in suture plane — 46 mm.; axial — 50 mm.

Form: Variable, ovoid to oblong.
*Symmetry.*—Usually symmetrical, nearly round in basal aspect.
*Suture.*—A narrow line extending from apex to base.
*Color.*—Red-purple (Plate 5-L-5), usually darker than surrounding blush color.
*Ventral surface.*—Rounded; sometimes slightly lipped on both sides, usually slightly asymmetrical.
*Stem cavity.*—Nearly round. Average width — 8 to 10 mm. Average length — 8 to 12 mm. Cavity somewhat abrupt and deep; average depth — 12 to 14 mm.
*Base.*—Rounded to very slightly truncate; occasionally slightly oblique to fruit axis.
*Apex.*—Variable from short to slightly elongate.
*Pistil point.*—Apical, usually slightly depressed.

Stem:
*Length.*—Average 18 to 20 mm.
*Color.*—Light green (Plate 19-I-2) to brown-green (Plate 13K-7).
*Caliper.*—1 to 1.5 mm.

Skin:
*Thickness.*—Medium. Tenacious to flesh until fully ripe. Slightly acid.
*Tendency to crack.*—None observed.
*Ground color.*—Yellow (Plate 10-J-5).
*Blush.*—Dark Red (Plate 7-L-5) to light red-orange (Plate 5-K-11), depending on maturity and degree of exposure to sunlight. Blush color covering 60 to 90 percent of fruit surface at maturity. Blush darkens and percentage of blush increases with advancing maturity. Apex and apical shoulders moderately flecked with yellow dots. Flecking less apparent over basal shoulders.
*Bloom.*—Medium, gray.

Flesh:
*Color.*—Light yellow-amber (Plate 9-J-6).
*Pit cavity.*—Slightly darker (Plate 10-K-7).
*Texture.*—Firm, fine.
*Juice.*—Juicy.
*Fibers.*—Few, fine, tender, medium length.
*Ripening.*—Even.
*Flavor.*—Sweet, mild, pleasant.
*Aroma.*—Slight.
*Eating quality.*—Good.

Stone: Clingstone, adheres to flesh over edges and sides of stone.
*Size.*—Medium to small; average length — 22.6 mm.; average width — 15.2 mm.; average breadth — 9.6 mm.
*Fibers.*—Short.
*Form.*—Variable, narrow oval to ovate.
*Base.*—Slightly truncate, usually oblique to stone axis, shorter on ventral suture side.
*Hilum.*—Small, narrow, oval.
*Apex.*—Acute to acuminate; tip variable but often quite sharp.
*Sides.*—Variable, usually unequal.
*Surface.*—Moderately grooved over basal shoulder, converging basally; surface of sides relatively smooth; usually one deep groove roughly parallel to and 2 to 3 mm. from ventral edge on both sides of stone.
*Ventral edge.*—Relatively thick with prominent wing from mid-point toward base.
*Dorsal edge.*—Deep groove from base to mid-suture; narrower, tight groove from mid-suture to apex.
*Color.*—Buff, (Plate 11-B-3).
*Splitting tendency.*—None observed.

Use: Fresh market for local and long distance shipping.
Keeping quality: Good.
Shipping Quality: Not established.
Resistance to insects and disease: No particular susceptibilities noted.

Although the new variety of plum tree possesses the described characteristics under the growing conditions prevailing in Tulare, County, Calif., in the central portion of the San Joaquin Valley, it is to be understood that variations of the usual magnitude in characteristics incident to changes in growing conditions, fertilization, pruning and pest control are to be expected.

Having described my new variety of plum tree, what I claim as new is:

1. A new and distinct variety of plum tree substantially as illustrated and described, broadly characterized by its general similarity to the unpatented Casselman Plum Tree, which it most nearly resembles and of which it is believed to be a sport but from which it is distinguished as to novelty by its fruit ripening four to five weeks later than that of the Casselman Plum Tree.

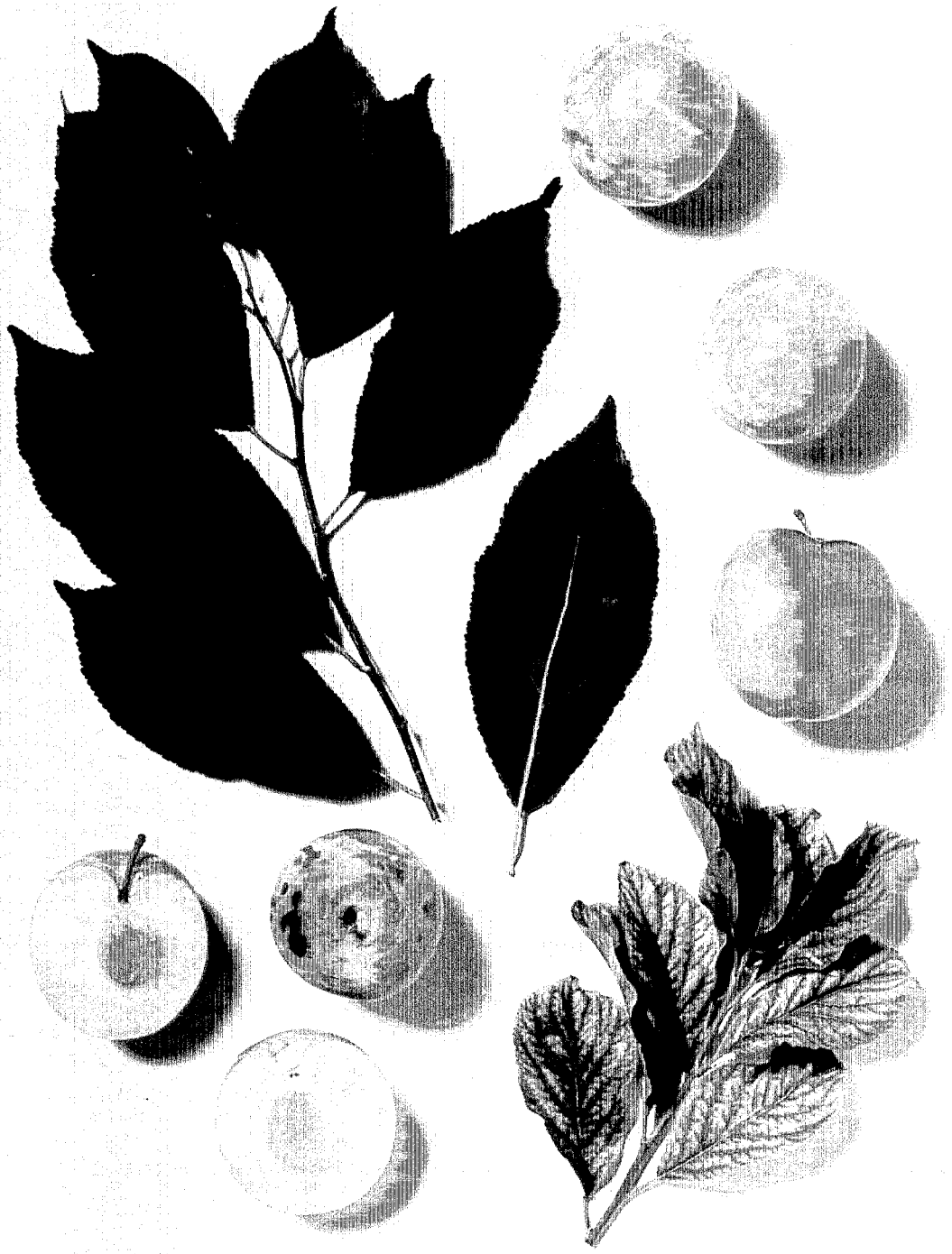

* * * * *